(12) United States Patent
Douglas et al.

(10) Patent No.: US 7,229,408 B2
(45) Date of Patent: Jun. 12, 2007

(54) LOW PROFILE SURGICAL RETRACTOR

(75) Inventors: Peter Douglas, New Milford, NJ (US);
Hugo Vanerman, Aaist (BE)

(73) Assignee: Ethicon, Inc., Somerville, NJ (US)

( * ) Notice: Subject to any disclaimer, the term of this patent is extended or adjusted under 35 U.S.C. 154(b) by 237 days.

(21) Appl. No.: 10/881,502

(22) Filed: Jun. 30, 2004

(65) Prior Publication Data
US 2006/0004261 A1    Jan. 5, 2006

(51) Int. Cl.
*A61B 1/32*    (2006.01)
(52) U.S. Cl. ........................ 600/214; 600/216
(58) Field of Classification Search ........... 600/208, 600/214, 215, 219, 225, 233, 224, 216, 222
See application file for complete search history.

(56) References Cited

U.S. PATENT DOCUMENTS

| | | | |
|---|---|---|---|
| 5,195,505 A * | 3/1993 | Josefsen | 600/204 |
| 5,514,157 A * | 5/1996 | Nicholas et al. | 606/206 |
| 5,562,690 A | 10/1996 | Green et al. | |
| 5,810,721 A | 9/1998 | Mueller et al. | |
| 6,190,311 B1 | 2/2001 | Glines et al. | |
| 6,451,054 B1 | 9/2002 | Stevens | |
| 2005/0240083 A1 * | 10/2005 | Orban, III | 600/210 |

OTHER PUBLICATIONS

H. Dave, et al., A Self Retaining Atrial Spreader for Minimally Invasive and Robotically-Assisted Intracardiac Operations, Cardiothoracic Technique and Technologies IX, Abstract 144, p. 208, The 9th Annual CTT Meeting (Mar. 19, 2003).

* cited by examiner

*Primary Examiner*—Cary E. O'Connor
(74) *Attorney, Agent, or Firm*—Scully, Scott, Murphy & Presser

(57) ABSTRACT

A compact, low-profile surgical retractor (100) avoids the need for a bulky frame. The retractor includes retractor blade components (110, 120, 130, 140, 150, 160) joined pivotally. A cable (170) is guided by each retractor blade component. A winding mechanism (180), such as a spool, is carried by one of the retractor blade components (120) for winding up the cable to cause the retractor blade components to transition from a closed position to an open position. The winding mechanism may be actuated by a detachable handle (200). The retractor blade components may be unitary, injection-molded pieces. The retractor blade components may be fixed pivotally, such as by pins, or pivotally joined by living hinges. A less-invasive surgical method is also provided in which the retractor is inserted into the body through an incision.

33 Claims, 19 Drawing Sheets

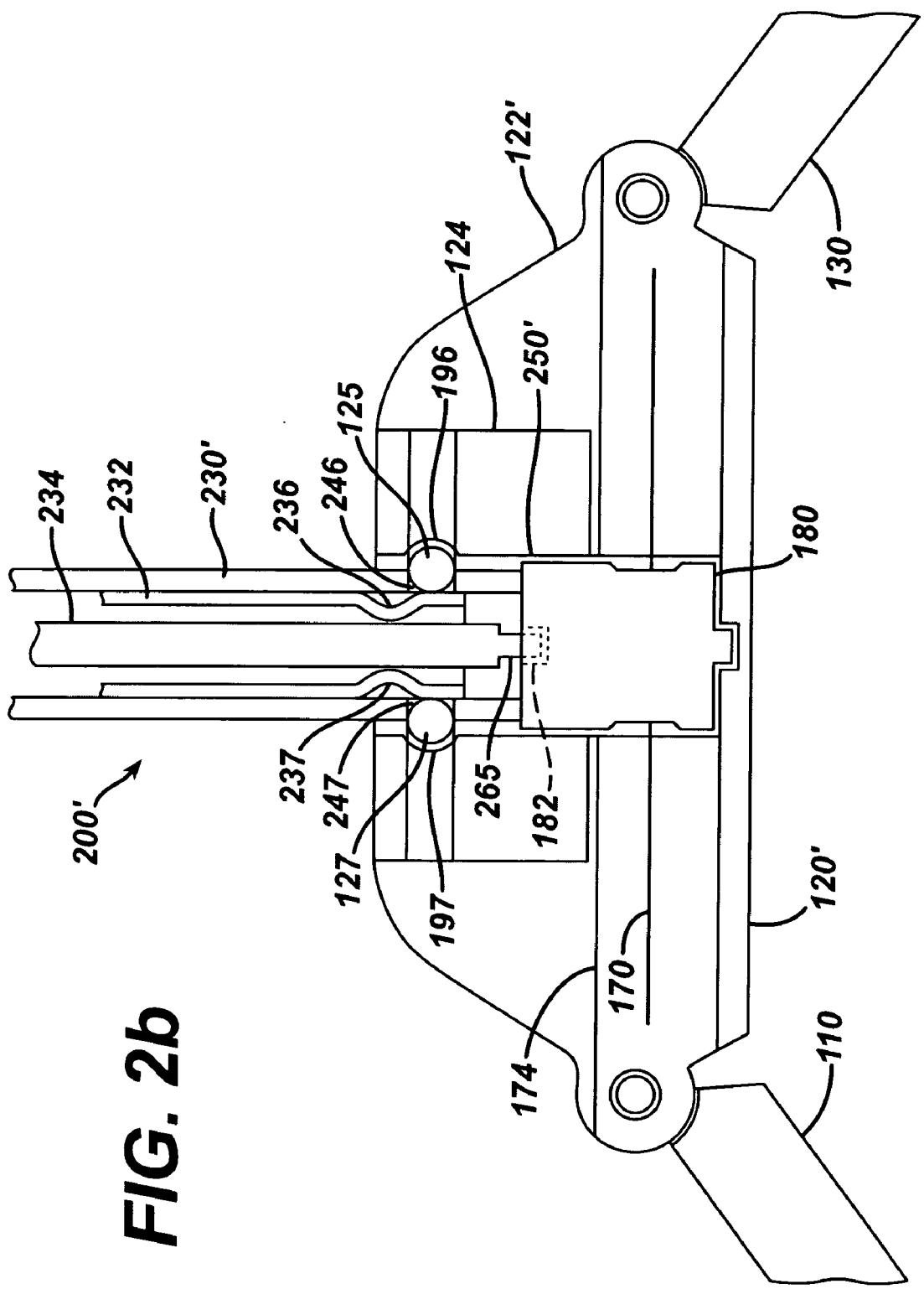

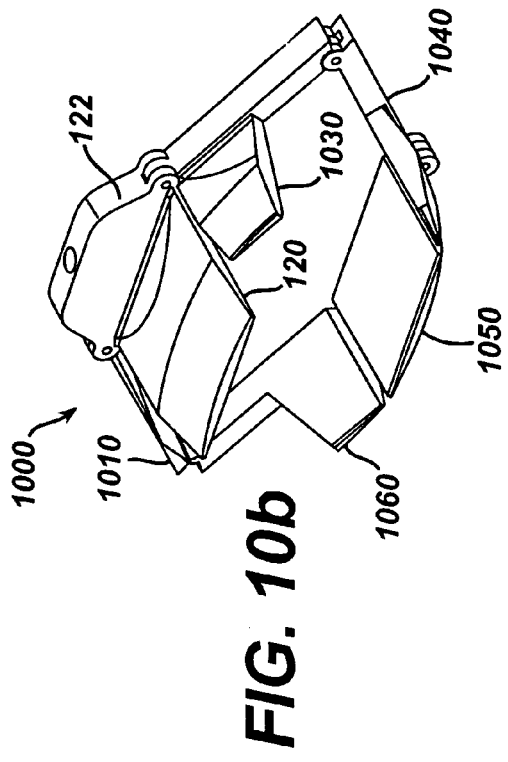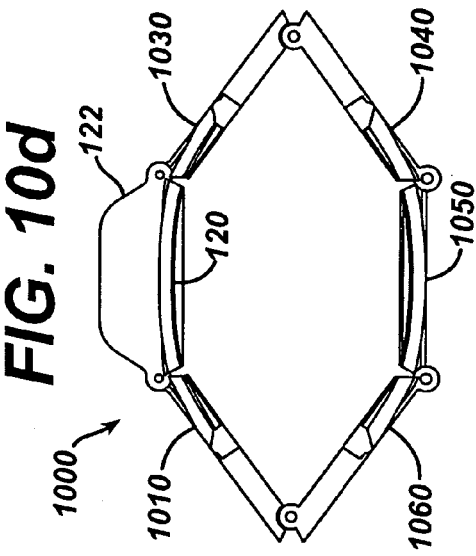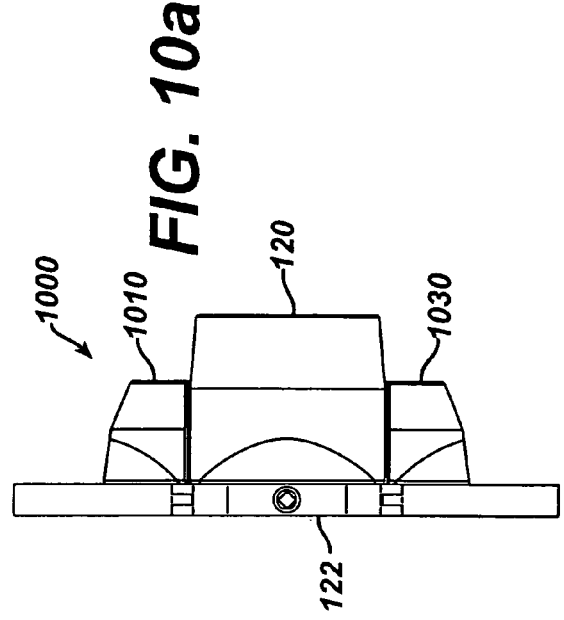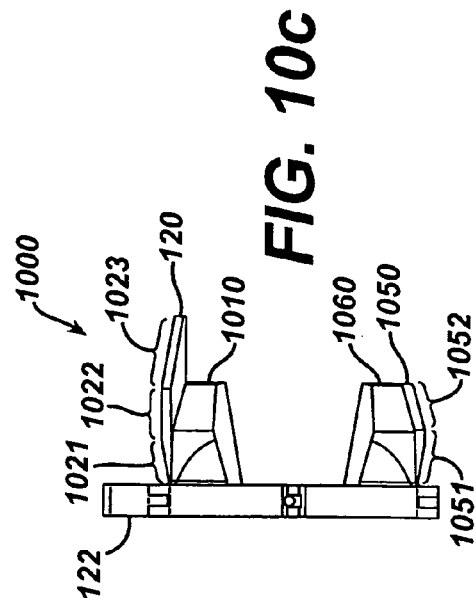

LOW PROFILE SURGICAL RETRACTOR

BACKGROUND OF THE INVENTION

1. Field of Invention

The invention relates to the field of medical instruments, and more particularly, to a low profile, compact retraction device that avoids the need for a bulky frame, and to surgical methods of using such a device.

2. Description of Related Art

Surgical retractors are frequently required, and equally commonly used, in surgical procedures to hold back the edges of superficial tissues and/or organs, allowing the surgeon to expose underlying anatomic structure to which she requires access. Conventional retractors are comprised of a stainless steel rack and pinion frame, with retractor blades mounted the frame, and a crank handle or similar means mounted to the frame or the blades in order to position the blades along the rack, opening and closing the retractor.

However, such retractors have the drawbacks that they tend to be large, bulky devices that occupy a considerable amount of space at the surgical site. This impedes the surgeon's access to and visualization of the surgical site, making any procedure more difficult and/or time consuming. On the other hand, it is advantageous to the patient to limit both the duration of the surgery and the size of the surgical site. Minimizing either or both is known to reduce the occurrence and/or severity of negative surgical ramifications that can lead to morbidity or mortality, and/or extended recovery periods. Towards that end, the medical arts have developed less invasive, minimally invasive and non-invasive surgical techniques. In such techniques, space at and around the surgical site is at a premium.

BRIEF SUMMARY OF THE INVENTION

Therefore, it would be advantageous to have a retraction device that performs the necessary functions of a conventional retractor without superfluous structure in the space outside the area being retracted. It would be further advantageous for such a device to be capable of inexpensive manufacture. The latter would make it economically feasible to use each device only once. Accordingly, this eliminates the need for cleaning and sterilization between uses, and the risk of microbial cross-contamination among subsequent users from inadequate cleaning and sterilization.

The invention described herein provides a low profile retractor that is designed to minimize the space occupied by the retractor. The blades and frame of the retractor can occupy the same space or be the same physical member, so that there will be few or no structural members outside the region being retracted. The blade members can be molded or machined separately and hinged together, or the blades can be attached as one piece and flex at the connection joints as a living hinge, e.g., when the blades are made of plastic. Additionally, the retractor can be easily inserted into the body via an incision for operations involving any type of retractor, e.g., atrial retraction.

In one aspect of the invention, a surgical retractor includes at least two retractor blade components joined pivotally, a cable, a deployed length of which is guided by the at least two retractor blade components, and a winding mechanism carried by at least one of the at least two retractor blade components for shortening the deployed length of the cable to cause the at least two retractor blade components to transition from a closed position to an open position.

In another aspect of the invention, a surgical retractor includes at least two banks of retractor blades, each of the at least two banks of retractor blades comprised of a plurality of articulated blade members comprising a deformable biocompatible material, a cable, a deployed length of which is at least partially guided by each of the at least two banks of retractor blades, and a winding mechanism carried by at least one of the at least two banks of retractor blades for shortening the deployed length of the cable to cause the at least two banks of retractor blades to deform from a closed position to an open position.

In another aspect of the invention, a surgical method includes inserting a retractor in a closed position into a body though a first incision in the body, wherein the retractor includes at least two retractor blade components joined pivotally, a cable, a deployed length of which is guided by the at least two retractor blade components, and a winding mechanism carried by at least one of the at least two retractor blade components, and operating the winding mechanism from a portion of a handle that is outside the body, where the handle is coupled to the winding mechanism, to shorten the deployed length of the cable to cause the at least two retractor blade components to transition from the closed position to an open position.

In another aspect of the invention, a surgical method includes positioning a retractor in an at least partially closed position for retracting tissue of a body, wherein the retractor includes at least two retractor blade components joined pivotally, a cable, a deployed length of which is guided by the at least two retractor blade components, a winding mechanism carried by at least one of the at least two retractor blade components, and a handle coupled to the winding mechanism, and operating the winding mechanism using the handle to shorten the deployed length of the cable to cause the at least two retractor blade components to transition from the closed position to an open position to retract the tissue.

The retractor may be used for any type of retraction procedure including sternotomy, thoracotomy, atrial retraction, abdominal retraction, and others.

BRIEF DESCRIPTION OF THE DRAWINGS

These and other features, advantages and benefits of the present invention will be made apparent through the following descriptions and accompanying figures, where like reference numerals refer to the same features across the various drawings, and wherein:

FIG. 2(b) shows a quick disconnect mechanism for a handle according to the present invention;

FIG. 10(a) shows a top view of a short blade retractor according to a fourth embodiment of the present invention;

FIG. 10(b) shows a perspective view of the short blade retractor according to the fourth embodiment;

FIG. 10(c) shows a side view of the short blade retractor according to the fourth embodiment;

FIG. 10(d) shows a front view of the short blade retractor according to the fourth embodiment;

DETAILED DESCRIPTION OF THE INVENTION

Figure 1A:
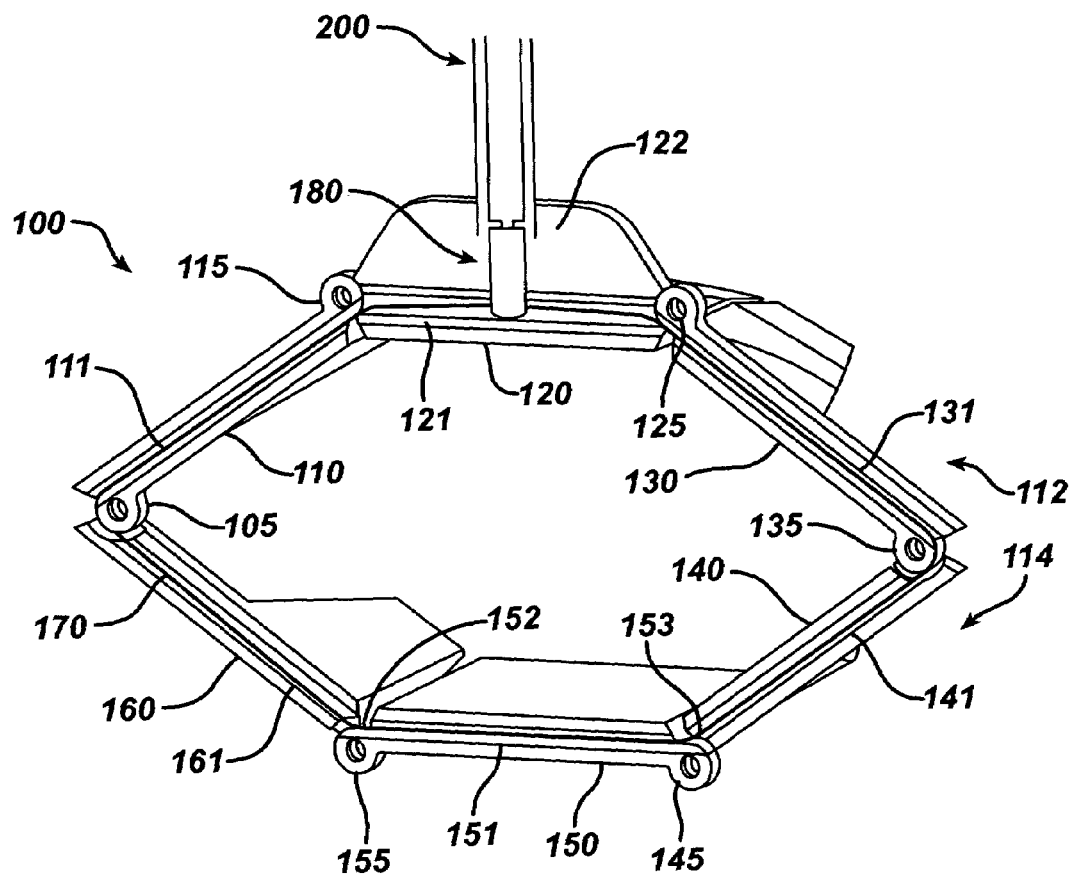
FIG. 1(a) shows a perspective cutaway view of a retractor according to a first embodiment of the present invention.

FIG. 1(a) shows a perspective cutaway view of a retractor according to a first embodiment of the present invention. The retractor 100 includes a number of retractor blade components 110, 120, 130, 140, 150 and 160, in this case six. Each of retractor blade components 110, 120, 130, 140, 150 and 160 are joined pivotally at pivot points 105, 115, 125, 135, 145 and 155, and together form a periphery of the retractor 100. The retractor blade components may be joined end to end, for instance. Neighboring retractor blade components may be separate components that are fixed together, e.g., by pins, or may be formed from a common material, in which case the pivot points may comprise living hinges. A living hinge generally includes a weakened, flexible area of material between neighboring retractor blade components.

A cable 170 has a deployed length that is guided by and/or through, or alternately attached to, one or more of the retractor blade components 110, 120, 130, 140, 150 and 160. In one possible design, both ends of cable 170 terminate at a winding mechanism 180, in this case a spool. The winding mechanism 180 may be carried by at least one of the retractor blade components, e.g., component 120. In particular, the retractor blade component 120 has a raised structure 122 for accommodating the winding mechanism 180. The distal end of a handle 200 can be inserted into the winding mechanism 180 and rotatably confined to the raised structure 122. Together, the handle 200 and winding mechanism 180 are operative to shorten the length of cable 170, guided by the blade components.

Figure 1B:
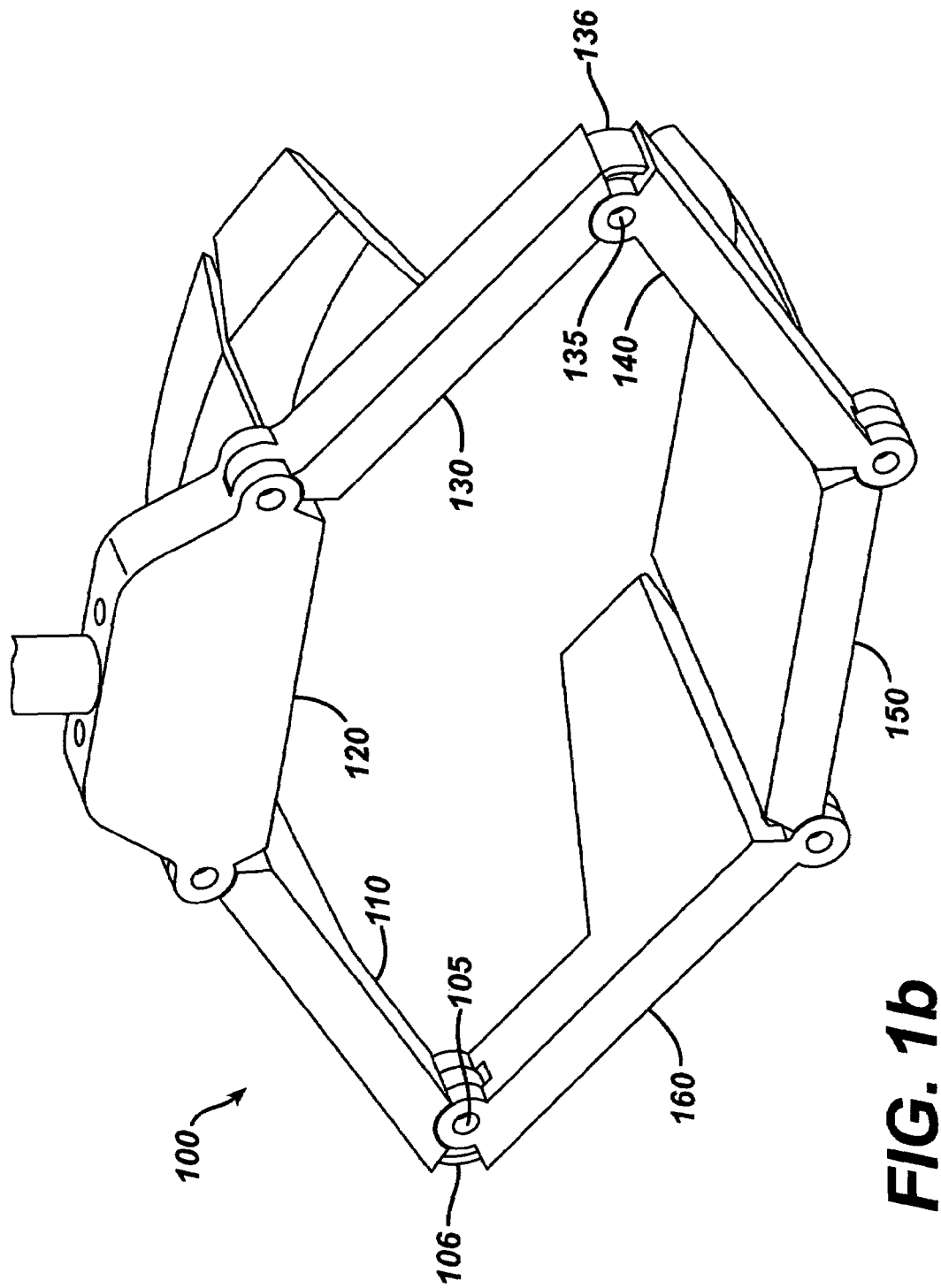
FIG. 1(b) shows a perspective view of the retractor according to the first embodiment of the present invention.
Figure 1C:
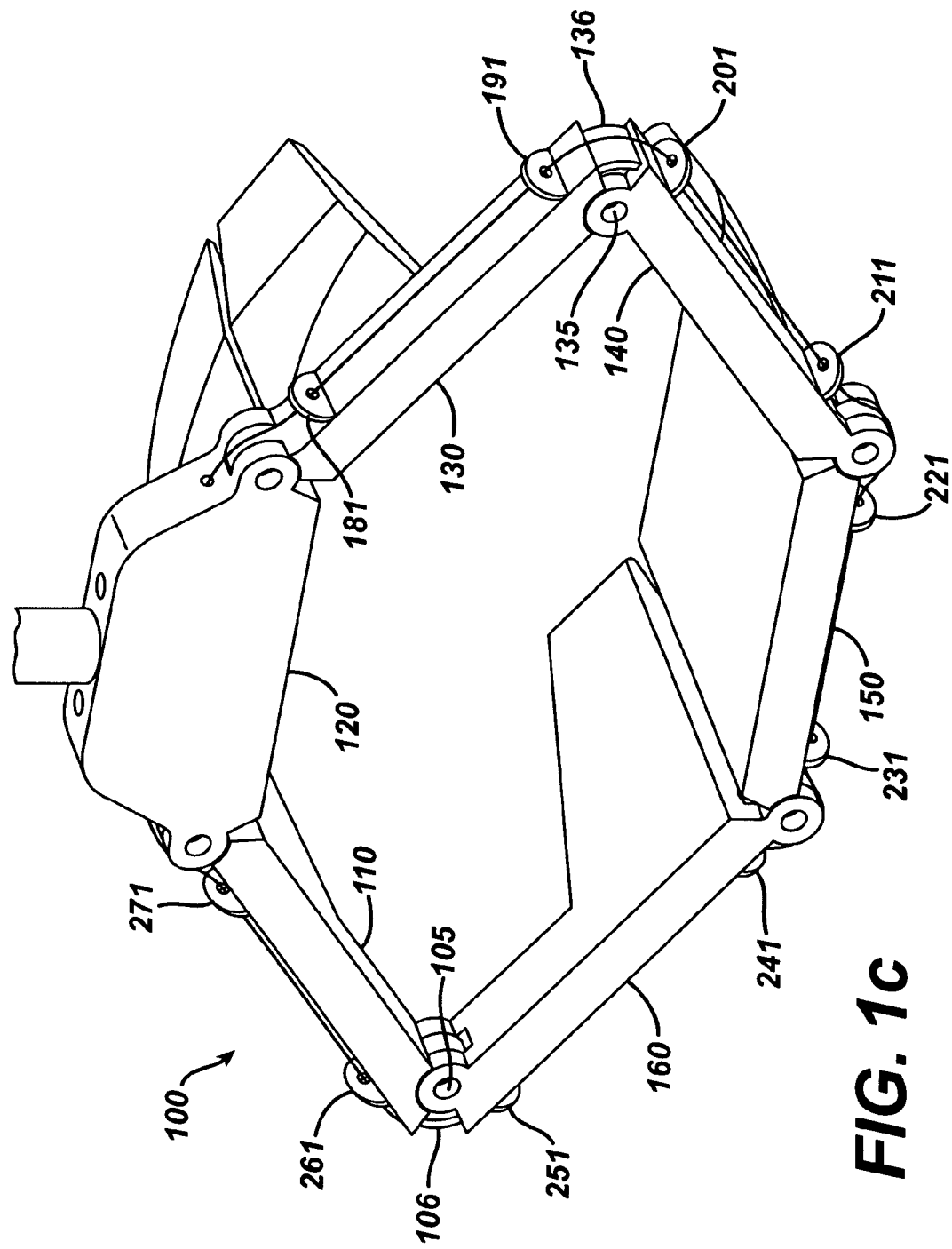
FIG. 1(c) shows a perspective view of the retractor according to a modification of the first embodiment of the present invention, having external flanges for guiding a cable.

The cable may be a stranded metal cable that is selected to provide sufficient strength and flexibility. The term "cable" is meant to encompass any flexible elongated member, including, e.g., a nylon cable, or a belt made of rubber, plastic, suture or other material which can be guided at least partly about the retractor 100 and have its length adjusted. The cable may extend substantially fully through, and be guided by, each retractor blade component 110, 120, 130, 140, 150 and 160 by providing generally straight or slightly arcuate passages in the retractor blade components, e.g., passages 111, 121, 131, 141, 151 and 161, respectively. Note that these passages can be seen in the cutaway view of FIG. 1. Holes can be provided at the ends of each retractor blade component for entry and exit, respectively, of the cable through the component. For example, for retractor blade component 150, holes 152 and 153 may be provided. The passages in the retractor blade components are preferably sized and have a smooth finish to allow the cable to slide within the retractor blade components without binding. Optionally, the cable 170 can extend through, and be guided by, structures such as eyelets, flanges, slots, apertures or the like on an outer or inner surface of the retractor blade components 110, 120, 130, 140, 150 and 160. For example, with reference to FIG. 1(c), the cable 170 may extend through flanges 181, 191, 201, 211, 221, 231, 241, 251, 261 and 271, on an outer surface of the retractor blade components.

In an alternate embodiment, the cable is guided by only some of the retractor blade components. For example, the cable 170 may be fastened to the winding mechanism 180 at one end, and to the retractor blade component 150 at the cable's other end, and routed so that the cable extends at least about one-half way around the retractor 100, or around n/2 joints, where n is the number of blades in the retractor 100. In another approach, two cables which each extend half way around the retractor 100 are provided, one on each side of the retractor. Both such cables are fastened at one end to the winding mechanism 180.

Figure 6:
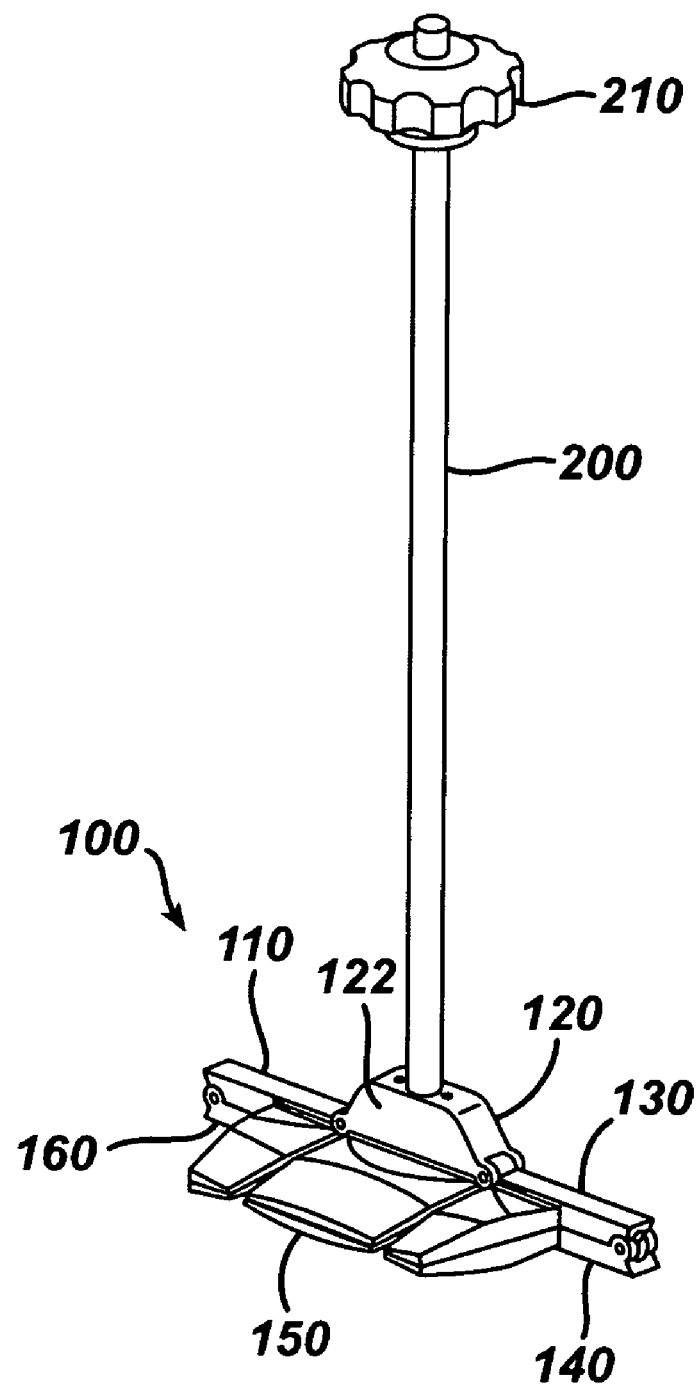
FIG. 6 shows a perspective view of a retractor in a closed position according to the first embodiment of the present invention.

The retractor 100 can be used during surgery to hold back the edges of tissues and organs to maintain exposure of the underlying anatomic parts or to otherwise hold the tissue in a desired position. Preferably, the retractor 100 may fold to a compact size, for example as shown in FIG. 6, so that the retractor blade components on opposing sides of the retractor are substantially parallel to one another and folded back to back. Referring back to FIG. 1(a), the retractor blade components 110, 120 and 130 on a top side 112 of the retractor 100, and the retractor blade components 140, 150 and 160 on a bottom side 114 of the retractor 100 can be configured to be substantially parallel when in the closed position.

More preferably, the retractor may be folded to a size more compact than the open position when in the closed position. Springs, such as bent flat springs 106 and 136 shown in FIG. 1(b), may be provided at the pivot points 105 and 135, respectively, to bias the retractor 100 toward a closed position. In particular, springs 106 and 136 may be provided at least at the pivot points that join the top 112 and bottom sides 114 of the retractor 100, e.g., pivot points 105 and 135, respectively. The springs can be provided at the pivot points using various approaches that will be apparent to those skilled in the art. For example, the two ends of a torsion or flat spring can be secured into slots, apertures or other constructs of the neighboring retractor blade components 110, 120, etc., of a pivot point 105, 115, etc. The springs are preferably set in a state that tends to close the retractor 100. For example, a flat spring 106, 136, may be set in a crimped state. When pins are used at the pivot points 105, 115, etc., the coiled portion of a torsion spring can be disposed about the pin. Alternately or additionally, the retractor blade components themselves may be flexible strips that provide a spring force. For example, two flat metal strips may be joined end to end. The strips are forced apart to an open position when cable 170 is wound by winding mechanism 180, and return to a closed position when the cable 170 is unwound.

Figure 2A:
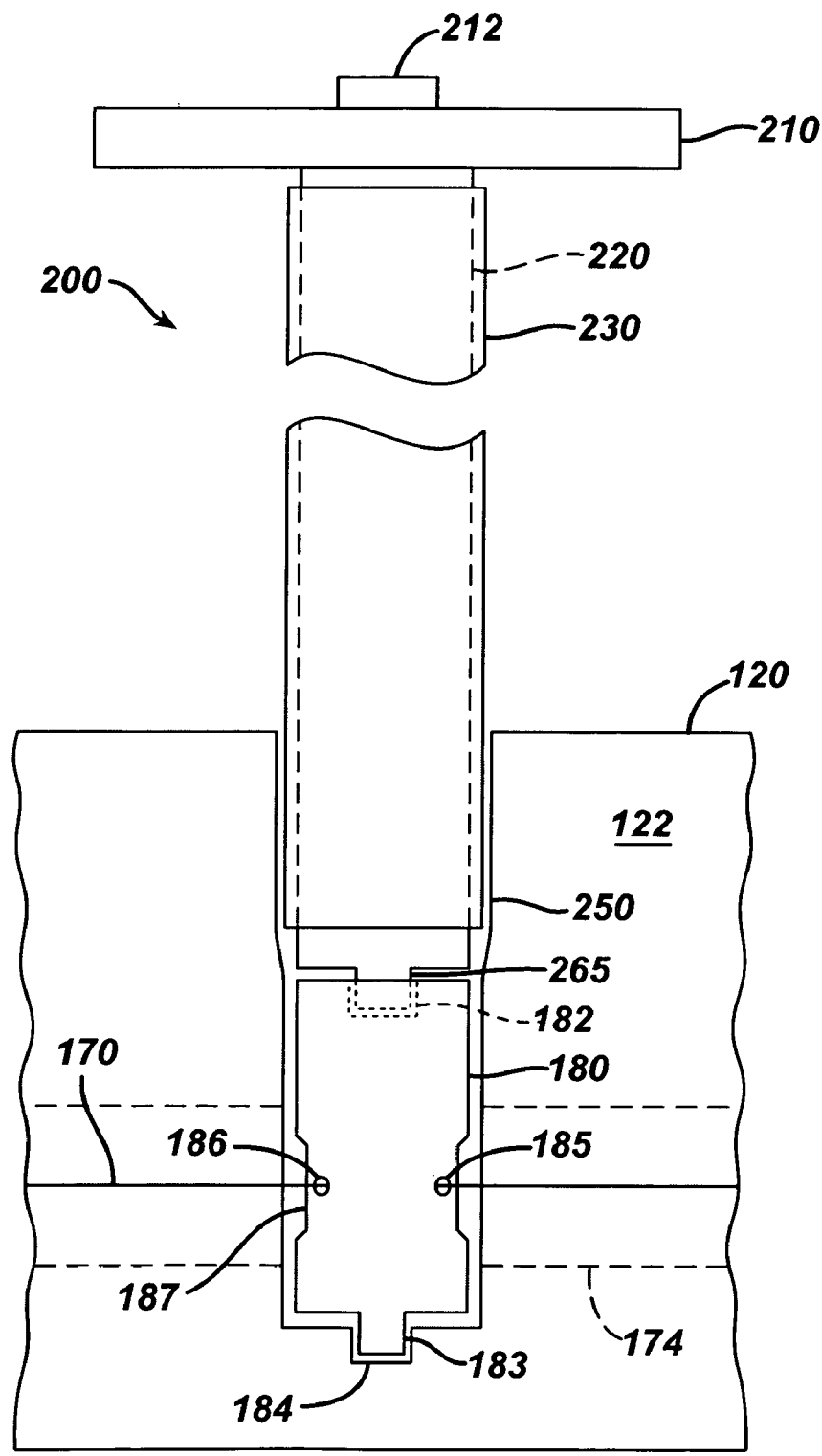
FIG. 2(a) shows a handle joined to a winding mechanism according to the first embodiment.

The compact size allows easy storage, shipping and transport of the retractor, as well as suitability with less-invasive surgical procedures, described further below. During use, the handle 200 is inserted into the winding mechanism 180 to wind up the cable 170, as discussed further in connection with FIG. 2(*a*). The turning action of the winding mechanism 180 shortens the length of the cable 170. This, in turn, causes the pivot points 105 and 135, which join the top 112 and bottom sides 114 of the retractor 100 to move toward one another, while the top side pivot points 115 and 125 move away from the bottom side pivot points 155 and 145, respectively. Thus, when the retractor is opened, the pivots points that join two sides of the retractor move radially inward, while the remaining pivot points move radially outward. Conversely, when the retractor is closed, the pivots points that join two sides of the retractor move radially outward, while the remaining pivot points move radially inward. The retractor 100 can thus be opened up to a desired size in a controlled manner. Note that the retractor 100 need not be opened to its full extent. It may be opened only partially depending on the surgical need. When open, the retractor may form a multi-sided structure such as a regular polygon. The retractor may be made in various sizes, e.g., diameters, as well for different applications. The overall ruggedness of the retractor, including, e.g., the thickness of its components, can be designed to withstand a specified retraction force.

Furthermore, the number of retractor blade components and their dimensions may be varied as needed for a particular application. Generally, at least two retractor blade components should be used. The retractor blade components may have different lengths, and an odd or even number of retractor blade components may be used. The retractor blade components may be configured to accept one or more instruments, such as stabilizers, light sources, saline sources, blowers, and misters, and may include structures such as suture stays molded into the blade components or attached thereto.

Preferably, each retractor blade component 110, 120, etc., will be unitary, i.e., fashioned in one piece. One means to achieve this is to form the retractor blade components with injection molded plastic. With minor assembly, the retractor 100 may be built at a cost that allows it to be disposable. Alternatively, the retractor blade components may include another biocompatible material, such as stainless steel. In another option, the retractor blade components include support or arm portions, which are pivotally joined, and blade portions, which are removably secured to the support portions, e.g., using screws, tabs in slots, or other known fastening structures. In this manner, different blade portions can be used depending on the surgical need.

FIG. 2(*a*) shows a handle 200 joined to a winding mechanism 180 according to the first embodiment, but is generally applicable to the other embodiments as well. The winding mechanism 180 is provided in the raised structure 122 of the retractor blade component 120. The cable 170 extends in a passageway 174 within the raised structure 122, and, in one approach, both of its ends are secured to the winding mechanism 180. For example, the winding mechanism 180 may be a hollow metal drum with apertures 185, 186, on two opposing sides, in which case the cable ends are attached to balls or other structures within the winding mechanism that are larger than the apertures 185, 186 to retain the cable ends therein. Alternately, apertures 185, 186 may be the ends of a passage through winding mechanism 180. The cable 170 may unitarily pass through the winding mechanism 180, and still be wound thereon as winding mechanism 180 is turned. In either case, the cable 170 may be at least partially wound around the winding mechanism 180 even in the closed position. Among the benefits of pre-winding the cable around the winding mechanism 180 is that the tension is consistently applied tangent to the winding mechanism 180. Accordingly, there is little to no variation in the force or displacement as the winding mechanism 180 spools the cable 170.

The winding mechanism 180 may rotate on a structure 183 that is seated in a corresponding structure 184 of the retractor blade component 120. For example, the structure 183 may be a threaded or a smooth cylindrical shaft. The winding mechanism 180 may have a recessed area 187 for gathering the cable 170 as it is wound. Extra space can be provided around the winding mechanism 180 as well for gathering the cable by shaping the opening 250 accordingly.

In one embodiment, the handle 200 can be inserted into, and detached from, the winding mechanism 180 as desired. That is, the handle 200 can be coupled to, and uncoupled from, the retractor. This is convenient during surgery, for example, to enable the retractor to be inserted via one incision in the body, while the handle is inserted via another incision and subsequently coupled to the retractor in situ. Alternately, the handle 200 can be inserted into the winding mechanism 180 to wind up the cable 170 until the retractor 100 has opened to any desired degree, and the handle 200 can then be removed while additional surgical procedures are conducted. When the retraction is no longer needed, the handle 200 can be reinserted into the winding mechanism 180 to unwind the cable 170, allowing the retractor 100 to close. Furthermore, adjustments to the retractor may be made during the course of the surgery to partially increase or decrease the amount it is opened to an extent that is less than the full range of motion.

The handle 200 may be elongated to allow adjustment of the retractor 100 without interfering with the surgical site. Optionally, the handle 200 is provided directly on one of the retractor blade components. Various mechanisms may be employed to allow the handle to engage the winding mechanism, and to enable winding and unwinding of the cable 170. Another consideration is that the retractor 100 should not open or close when the handle is removed or decoupled from the winding mechanism, i.e., the retractor should remain in the position it is in when the handle is decoupled from the winding mechanism. An appropriate locking mechanism for the winding mechanism can be provided using various techniques.

In one embodiment, the handle 200 includes an outer portion 230, which may be cylindrical tube, and an inner shaft 220, which is joined to a turn knob 210 via a ratchet mechanism to allow rotation only in one direction. The inner shaft 220 may include a projection, such as a square member 265, which is removably received in a socket 182 of the winding mechanism 180 when the distal portion, e.g., tip, of the handle 200 is inserted into the opening 250, such as a blind hole, in the retractor blade component 120. Moreover, the handle 200 may be designed to pivot with respect to the retractor blade component 120, e.g., by designing the raised structure 122 so it is pivotally joined to the retractor blade component 120, e.g., using a hinge to allow the handle 200 to be some angle between parallel and perpendicular with the retractor blade component 120. The hinge may be provided with detents as desired, for example at the parallel and/or perpendicular positions.

In an alternate embodiment, the handle 200 may have a tongue pivotally coupled to its distal end that is received in an aperture in the winding mechanism 180, such as the socket 182. For example, any of the mechanisms for connecting a handle to a holder as discussed in U.S. Pat. No. 6,451,054, incorporated in its entirety for all purposes herein by reference, may be used.

Alternately or additionally, the handle may be secured to the retractor blade component using any of various possible structures. For example, a quick disconnect mechanism as shown in FIG. 2(b) may be used. In this design, a modified handle 200' includes an outer sleeve or portion 230', an inner sleeve 232, and a shaft 234 with a projection 265 that is removably received in the socket 182 of the winding mechanism 180 to wind the cable 170 in the passageway 174.

An insert 124 in the raised structure 122' of the retractor blade component 120' includes an opening 250' with cup-shaped recesses 196 and 197. When the handle 200' is outside the opening 250', and a push button 212 that controls movement of the inner sleeve 232 is in an unlocked position, cup-shaped recesses 236 and 237 formed in the inner sleeve 232 are even with circular openings 246 and 247, respectively, formed in the outer sleeve 230'. As an alternative to the cup-shaped recesses 236 and 237, a single circumferential recess may be used. Balls 126 and 127 are retained within the outer sleeve 230' since the openings 246 and 247 are slightly smaller than the diameter of the balls 126 and 127.

When the handle 200' is inserted into the opening 250', the balls 126 and 127 are forced inward by the walls of the opening 250' into the cup-shaped recesses 236 and 237, respectively, permitting the projecting member 265 to reach and engage the socket 182. The push button 212 is then moved to a locking position, causing the inner sleeve 232 to move upward to the position shown in FIG. 2(b). It is also possible to configure the handle 200' so that the inner sleeve 232 moves downward in the locking position. In either case, the outer surface of the inner sleeve 232 forces the balls 126 and 127 to move radially outward through the circular openings 246 and 247, respectively, and into the cup-shaped recesses 196 and 197, respectively, of the insert 124, thereby securing the outer sleeve 230' of the handle 200' to the retractor blade component 120'. The surgeon can therefore grasp the handle 200' without it being pulled out from the retractor or twisted with respect to the retractor.

To remove the handle, the push-button is moved to the unlocked position so that the inner sleeve 232 is moved back to the position wherein the cup-shaped recesses 236 and 237 are even with the circular openings 246 and 247, respectively, thereby allowing the balls 126 and 127 to move radially inward to allow the handle 200' to be withdrawn. Preferably, two or more circumferentially arranged balls and cup-shaped recesses are used, though only one is sufficient. Various other quick connect and disconnect mechanisms may be used as will be appreciated by those skilled in the art.

Referring again to FIG. 2(a), in a further option, the outer portion 230 of the handle 200 may include a threaded portion (not shown) that is threaded into a corresponding threaded portion of the opening 250. In yet another option, a friction fit may be used, e.g., where raised structures are arranged circumferentially about the outer portion 230 of the handle 200, and corresponding receiving structures, such as dimples, are located circumferentially about the opening 250. In use, the surgeon or other user pushes the handle 200 into the opening 250 and rotates it until the raised structures are seated in the receiving structures. The handle can be removed by pulling it out of the opening 250.

In any event, in the embodiment shown in FIG. 2(b), the outer portion 230 of the handle 200 is secured non-rotatably to the retractor blade component 120, and the inner shaft 220 can be rotated to control the winding and unwinding of the cable 170 via the turn knob 210. The outer portion 230 of the handle 200 may be gripped by the user during use to guide and position the retractor.

Figure 2C:
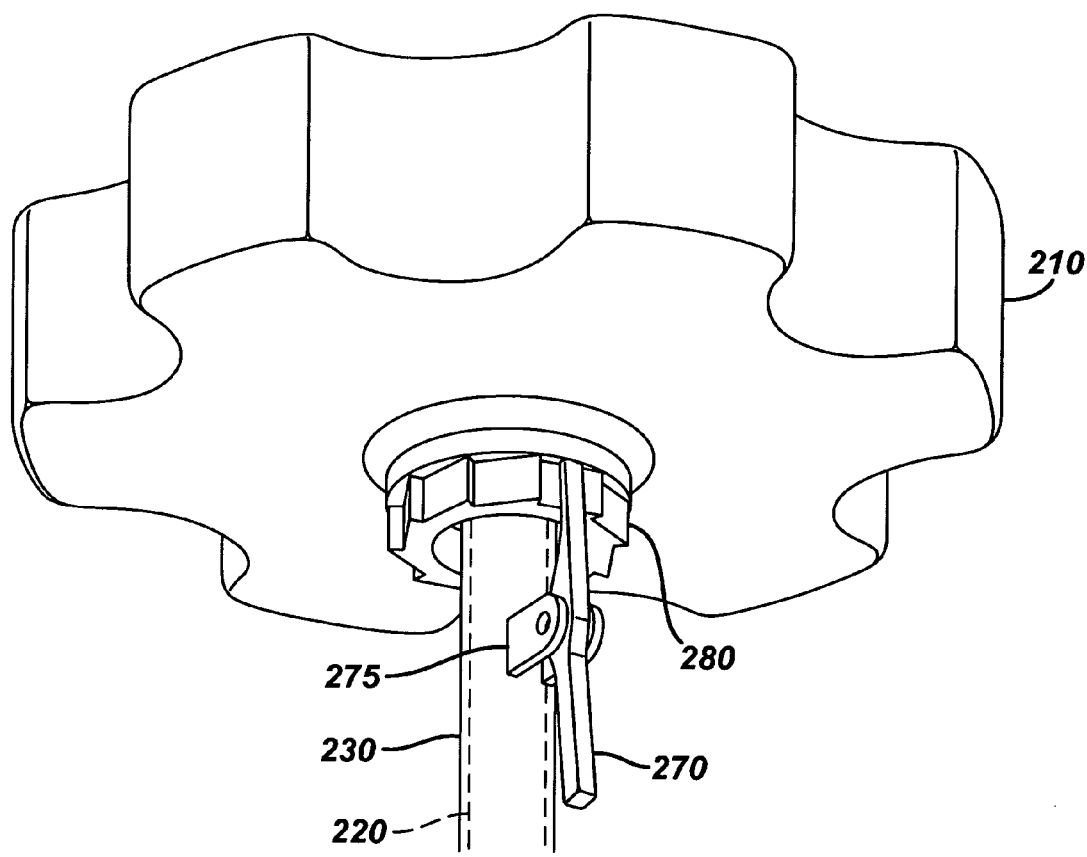
FIG. 2(c) shows a ratchet mechanism of a handle according to the present invention.

FIG. 2(c) shows a ratchet mechanism of a handle according to the present invention. The ratchet mechanism includes a finger-operated release arm 270, which engages a gear 280 that is coupled to rotate with the turn knob 210. The gear 280 may be formed by teeth that are molded onto the bottom of the turn knob 210, for example. The finger-operated release arm 270 may pivot about a pin held in a mounting bracket 275. The finger-operated release arm 270 is biased against the gear 280, for example by a torsion spring on the pin. The teeth of gear 280 allow the inner shaft 220 to rotate in one direction only, such as the direction to reduce the deployed length of the cable, when the finger-operated release arm 270 is engaged. In the example shown, the turn knob 210 can be rotated clockwise when viewed from the user's perspective to reduce the deployed length of the cable and thereby open the retractor. The turn knob 210 is coupled to the inner shaft 220, which is in turn coupled to the winding mechanism 180 when the handle 200 is inserted into the retractor blade component 120.

When the finger-operated release arm 270 is disengaged, the turn knob 210 can be rotated in the opposite direction to increase the deployed length of the cable, and thereby close the retractor. As discussed, springs may be provided at the pivot points of the retractor to bias the retractor toward a closed position. This provides a force on the cable that tends to unwind the cable. The ratchet mechanism prevents this unwinding when the finger-operated release arm 270 is engaged. Various other designs may be used. For example, a ratchet mechanism may be located in the winding mechanism rather than on the handle 200.

Figure 3:
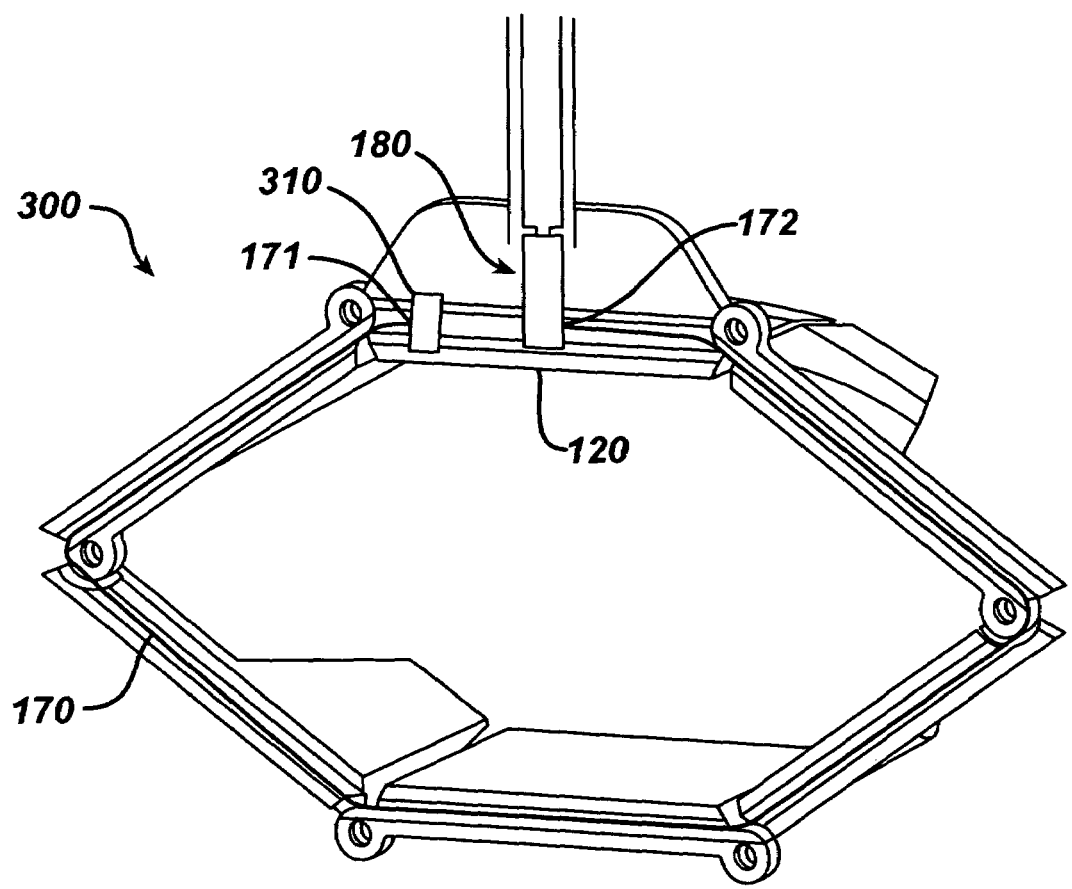
FIG. 3 shows a perspective cutaway view of a retractor according to a second embodiment of the present invention.

FIG. 3 shows a perspective cutaway view of a retractor 300 according to a second embodiment of the present invention. Here, one end 171 of the cable 170 terminates at a fixed point, such as at a ball or block structure 310, which is carried by the retractor blade component 120. The other end 172 of the cable 170 is attached to the winding mechanism 180. In this approach, only one end of the cable is wound up by the winding mechanism 180, so twice as many rotations of the turn knob are required compared to the embodiment of FIGS. 2(a) and 2(c) to achieve the same amount of winding or unwinding. This may be desirable since it provides a finer control of the winding and unwinding. Note that, in this and other embodiments, gearing may be used so that the rotation of the turn knob 210 relative to the winding mechanism 180 is greater than or less than 1:1.

Figure 4:
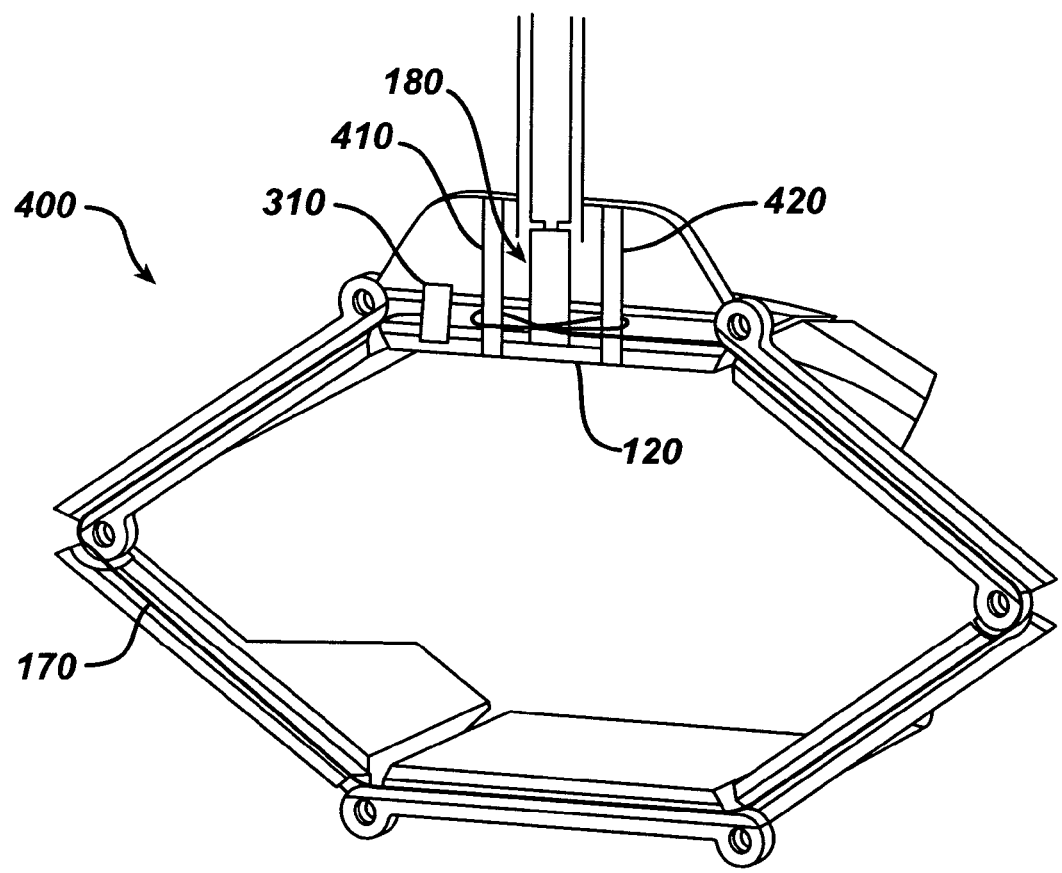
FIG. 4 shows a perspective cutaway view of a retractor according to a third embodiment of the present invention.

FIG. 4 shows a perspective cutaway view of a retractor 400 according to a third embodiment of the present invention. Here, one end of the cable 170 remains attached to the fixed structure 310, while the other end of the cable is wound around posts or winding pins 410 and 420 which are arranged in the retractor blade component 120, before terminating at the winding mechanism 180. Due to the 180-degree turns about the pins 410 and 420, a moderate amount of friction between the cable 170 and the pins 410 and 420 that prevents the cable from unwinding due to the force of the retracted tissue, yet still allows the cable to be wound up or unwound by the turn knob 210 with relative ease. Such an approach avoids the need for a ratchet mechanism to prevent the retractor from closing, e.g., when the handle is removed from the retractor blade component 120. The amount of friction will depend on factors such as the size and material of the cable 170 and pins 410 and 420, and the number of turns of the cable 170 about the pins 410 and 420.

Figure 5:
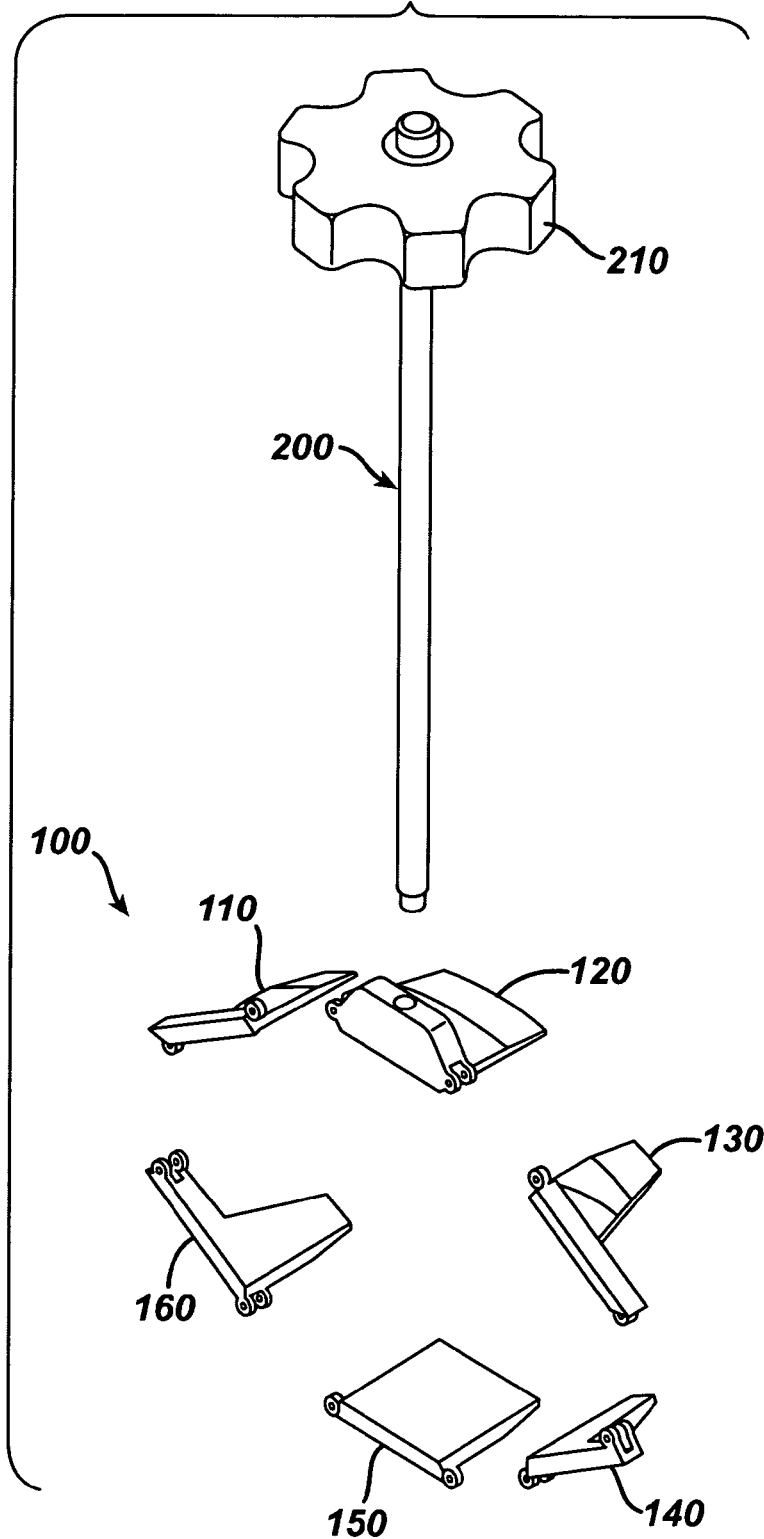
FIG. 5 shows an exploded perspective view of a retractor according to one of the foregoing embodiments of the present invention.

FIG. 5 shows an exploded perspective view of the retractor 100 according to a one embodiment of the present invention. The retractor 100 is shown in the open position with six retractor blade components 110, 120, 130, 140, 150 and 160.

Figure 7:
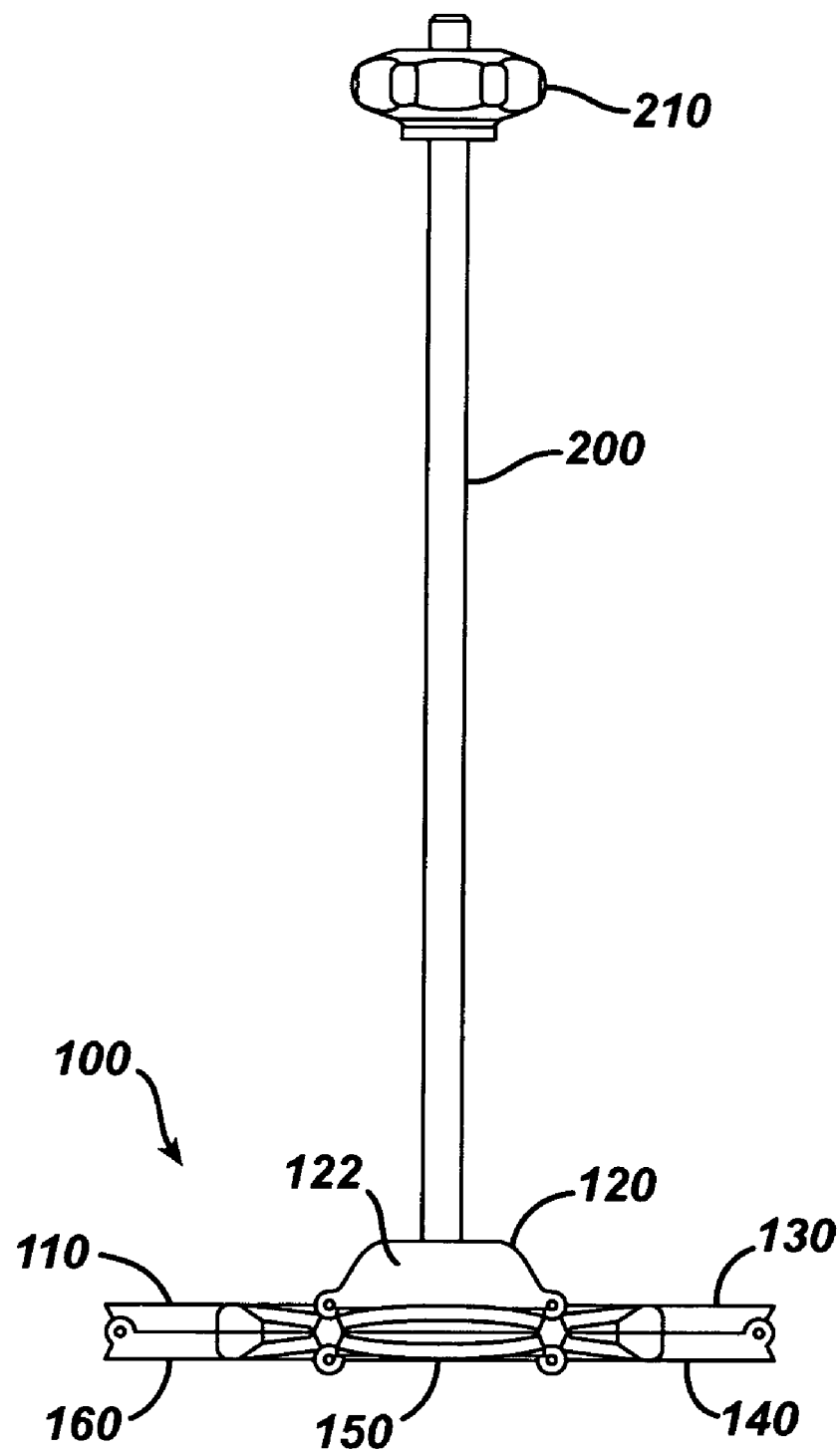
FIG. 7 shows a front view of a retractor in a closed position according to the first embodiment of the present invention.

FIG. 6 shows a perspective view of the retractor 100 in a closed position according to an embodiment of the present invention, while FIG. 7 shows a front view thereof. As mentioned, the retractor 100 folds to a compact size when not in use so that the retractor blade components on top and bottom sides of the retractor 100 are substantially parallel to one another and folded back to back. The retractor 100 is shown with retractor blade components 110, 120, 130, 140, 150 and 160, the raised structure 122 of retractor blade component 120, handle 200 and turn knob 210.

Figure 8:
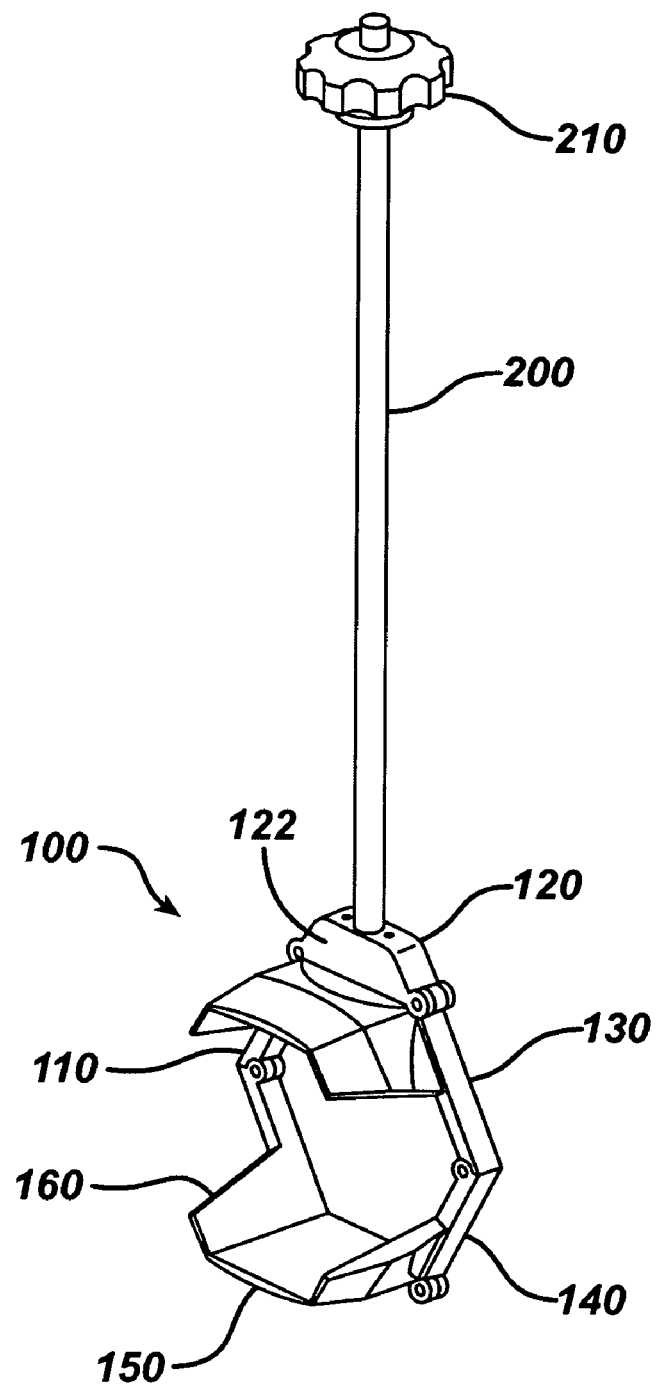
FIG. 8 shows a perspective view of a retractor in an open position according to the first embodiment of the present invention.
Figure 9:
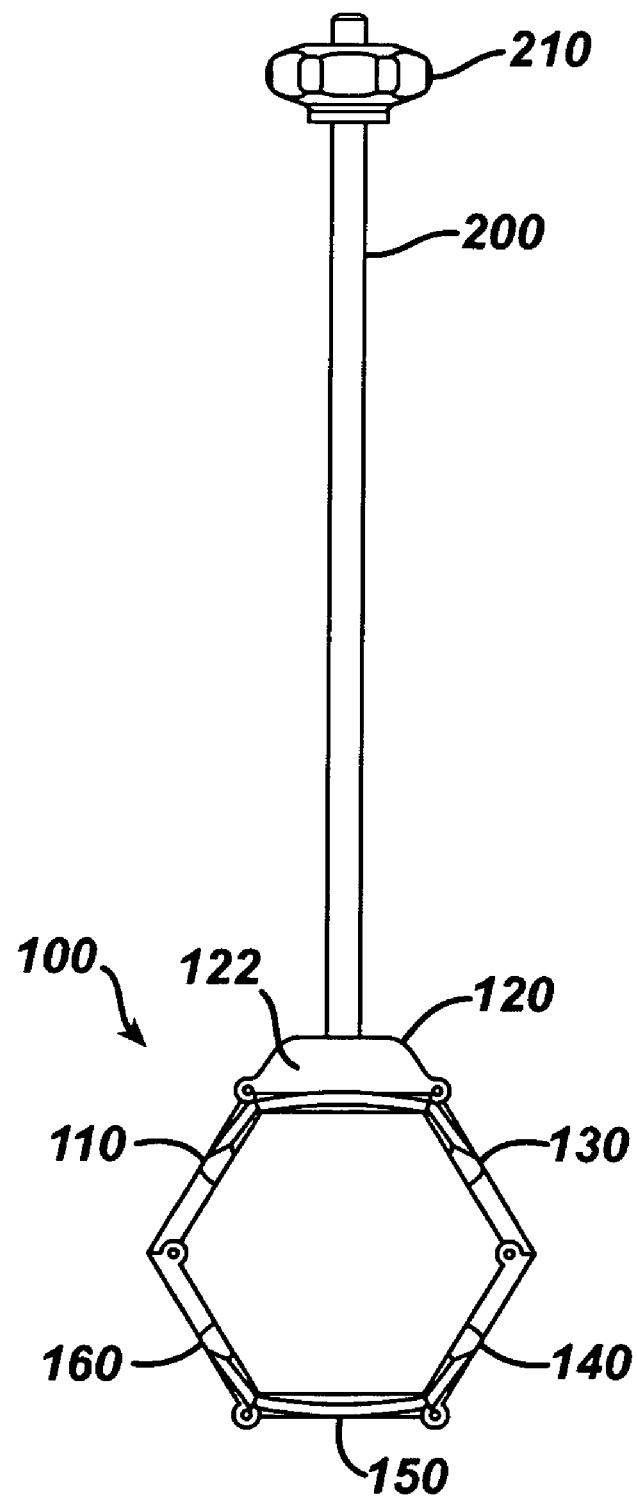
FIG. 9 shows a front view of a retractor in an open position according to the first embodiment of the present invention.

FIG. 8 shows a perspective view of the retractor 100 in an open position according to an embodiment of the present invention, while FIG. 9 shows a front view thereof. Note that the opening provided between the retractor blade components allows good access to the surgical site. The retractor 100 is shown with retractor blade components 110, 120, 130, 140, 150 and 160, the raised structure 122 of retractor blade component 120, handle 200 and turn knob 210.

FIG. 10(a) shows a top view of a short blade retractor 1000 according to a fourth embodiment of the present invention, while FIG. 10(b) shows a perspective view thereof, FIG. 10(c) shows a side view thereof, and FIG. 10(d) shows a front view thereof. In this short blade design, the retractor blade components 1010, 1030, 1040, 1050 and 1060 are shorter than the corresponding retractor blade components 110, 130, 140, 150 and 160 of the retractor 100 of FIG. 1, while blade 120 is of a similar size. Generally, lengths of the retractor blade components can vary and need not all be equal. This arrangement may be more suitable for some surgical applications. The retractor blade component 120, including raised structure 122, is the same as in the earlier embodiments, but its size may be adjusted as well as desired. Generally, the size, shape and other characteristics of each retractor blade component may be optimized for the particular application.

Note from FIG. 10(c) in particular that the retractor blade components may be shaped to optimally hold the retracted tissue. For example, a retractor blade component may include a portion that slopes radially inward toward the base end of the retractor blade component to assist in holding the retracted tissue. Retractor blade component 120 includes such a sloping portion 1021. A portion 1022 is generally parallel to the surgical site, while a portion 1023 slopes radially inward toward the free end of the retractor blade component. For the retractor blade component 1050, a portion 1051 slopes radially inward toward the base end of the retractor blade component, while a portion 1052 slopes radially inward toward the free end. The use of a portion that slopes radially inward toward the base end tends to assist in holding the retracted tissue by presenting an upward slope or increasing diameter to the tissue for movement toward the free end. An additional holding force can be obtained using a vacuum applied to apertures in the retractor blade components.

Figure 11A:
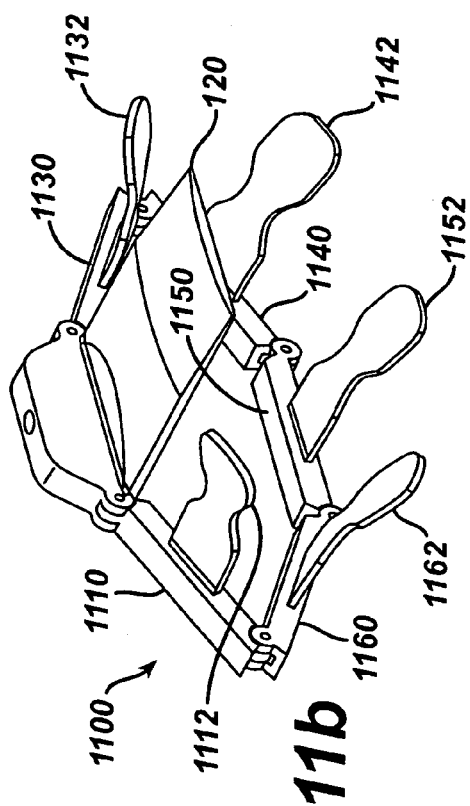
FIG. 11(a) shows a top view of a retractor with malleable blades according to a fifth embodiment of the present invention.
Figure 11B:
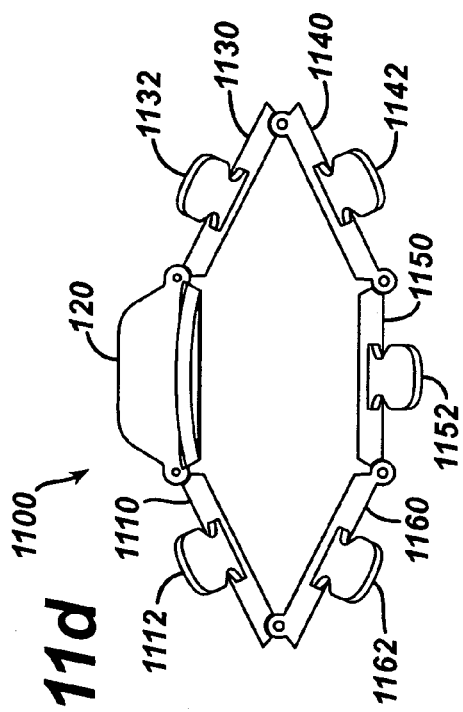
FIG. 11(b) shows a perspective view of the retractor with malleable blades according to the fifth embodiment.
Figure 11C:
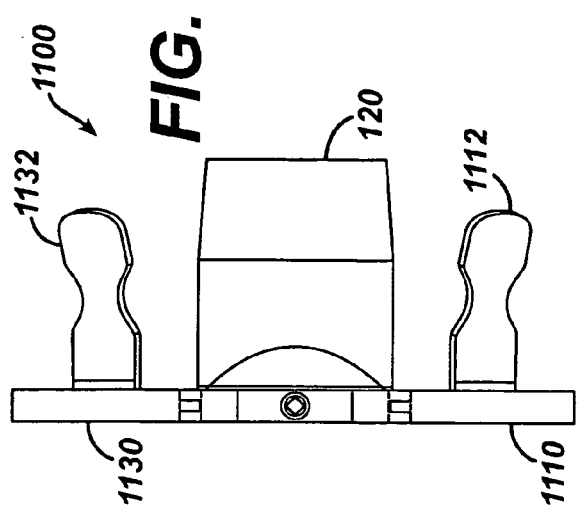
FIG. 11(c) shows a side view of the retractor with malleable blades according to the fifth embodiment.
Figure 11D:
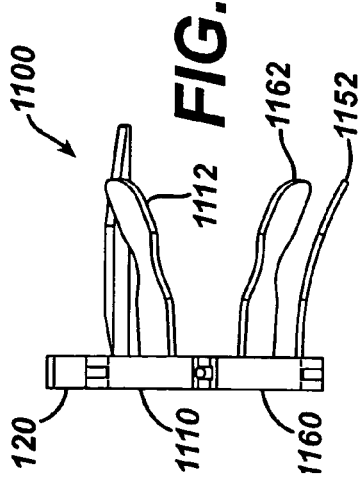
FIG. 11(d) shows a front view of the retractor with malleable blades according to the fifth embodiment.

FIG. 11(a) shows a top view of a retractor with malleable blades according to a fifth embodiment of the present invention, while FIG. 11(b) shows a perspective view thereof, FIG. 11(c) shows a side view thereof, and FIG. 11(d) shows a front view thereof. The retractor blade components include arms with tab-like blades. For example, arms 1110, 1130, 1140, 1150 and 1160 include tab-like blades 1112, 1132, 1142, 1152 and 1162, respectively. The retractor blade components may be unitary, i.e., formed in one-piece, or have separate arms and blades that are secured to one another. Moreover, the retractor blades 1112, 1132, 1142, 1152 and 1162 may be formed of a malleable material such as fully annealed metal that allows them to be bent to assume a desired shape. Advantageously, during surgery, the tabs can be shaped to securely hold back tissue and provide optimal access to the surgical site.

Figure 12:
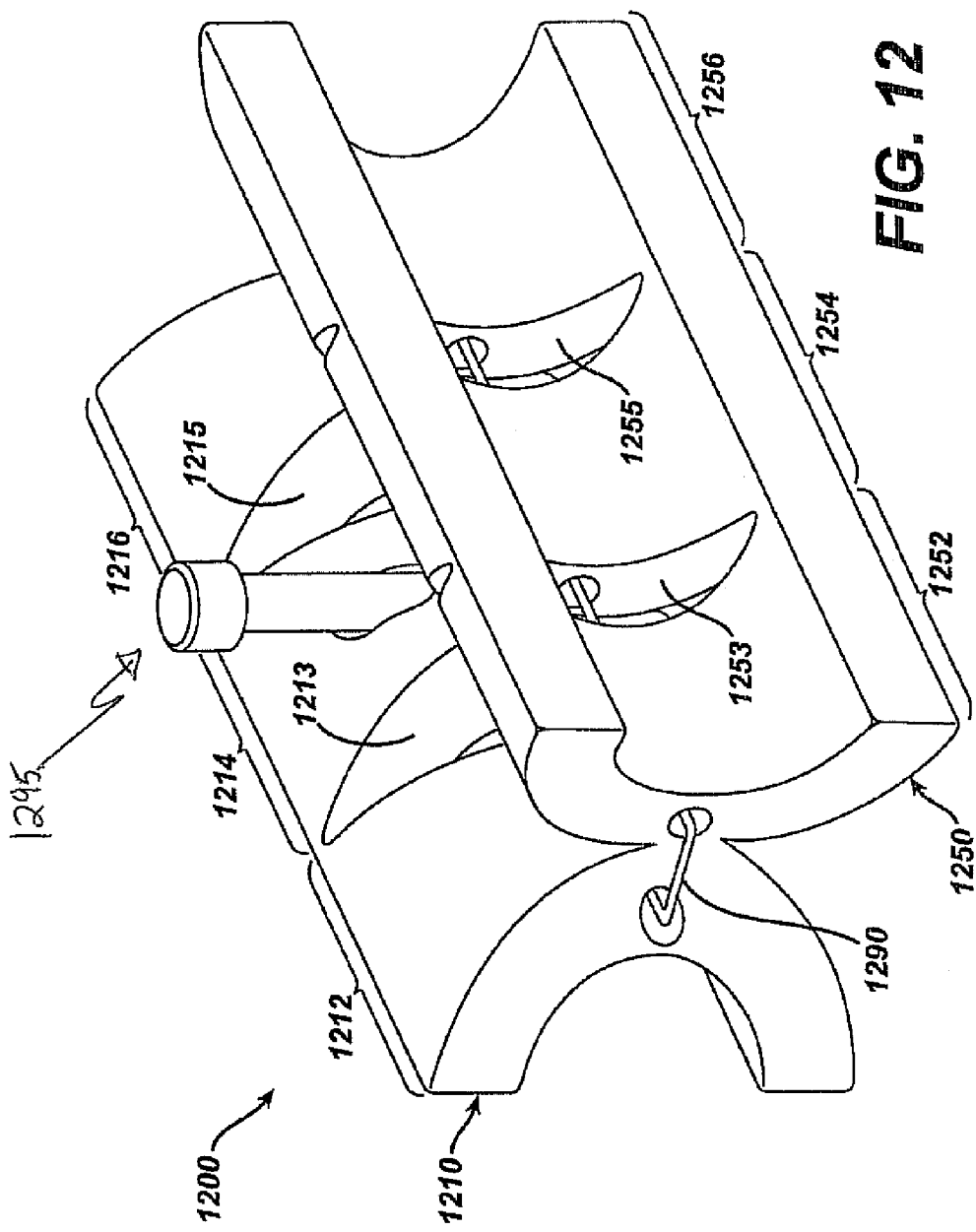
FIG. 12 shows a perspective view of a retractor according to a sixth embodiment of the present invention.

FIG. 12 shows a perspective view of a retractor according to a sixth embodiment of the present invention. The retractor 1200 includes at least two banks 1210, 1250 of retractor blades. Each bank is comprised of a bio-compatible material such as plastic or other polymer having a plurality of articulated blade members. For example, bank 1210 includes retractor blades 1212, 1214 and 1216, while bank 1250 includes retractor blades 1252, 1254 and 1256. The banks 1210, 1250 may be generally arc-shaped, e.g., as hollow half cylinders.

A cable 1290 extends through each bank or is otherwise guided by each bank, at least in part. A winding mechanism 1295, such as a bolt or other thread member that is threaded into one of the banks 1210, is provided for reducing the deployed length of the cable 1290 to cause the banks 1210, 1250 to deform from a closed position to an open position to retract tissue. The winding mechanism may be carried by one of the bank 1210, 1250. The cable 1290 is threaded into the winding mechanism 1295 in a manner such that when the mechanism 1295 is rotated, the cable 1290 is wound up on the shaft of the winding mechanism, causing the deployed length of the cable to become shorter. The banks 1210, 1250 may be pre-biased toward the open position to allow a direction for the retractor blades 1212, 1214, 1216, 1252, 1254 and 1256 to bend in when the deployed length of the cable 1290 is shortened.

The winding mechanism 1295 may be provided with a turn knob to allow it to be moved by hand. In FIG. 12, the retractor 1200 is in a closed position, and the banks 1210, 1250 are positioned substantially back to back. In an open position, the banks 1210 and 1250 would deform to form a roughly circular opening. The banks 1210, 1250 can each deform to a generally half circular shape without breaking or cracking, and return to the relaxed, resting position as shown at 1213, 1215 and 1253, 1255, respectively. A generally circular opening can thus be formed by the deformed banks 1210, 1250. This opening may be used to gain access to an underlying surgical site or to otherwise hold tissue in a desired position.

In one approach, the cable 1290 extends lengthwise through a midpoint of each bank, at least in part. In another approach, parallel first and second cables are provided above and below the midpoint of the banks 1210 and 1250. This approach can avoid upward or downward bending of the banks 1210, 1250 when the force on the banks is not at the midpoint, e.g., when the force of retracted tissue is mainly at the lower part of the banks 1210 and 1250. Both cables can be wound up by the winding mechanism 1295, or separate winding mechanisms may be used for each cable. For at least one of the banks 1210, 1250, the retractor blades are separated by living hinges formed, e.g., by slits or cut outs 1213, 1215, 1253 and 1255, which allow the respective bank to deform. In another option, one or more of the retractor blades 1212, 1214, 1216, 1252, 1254, and 1256 are completely detached from one another.

Figure 13:
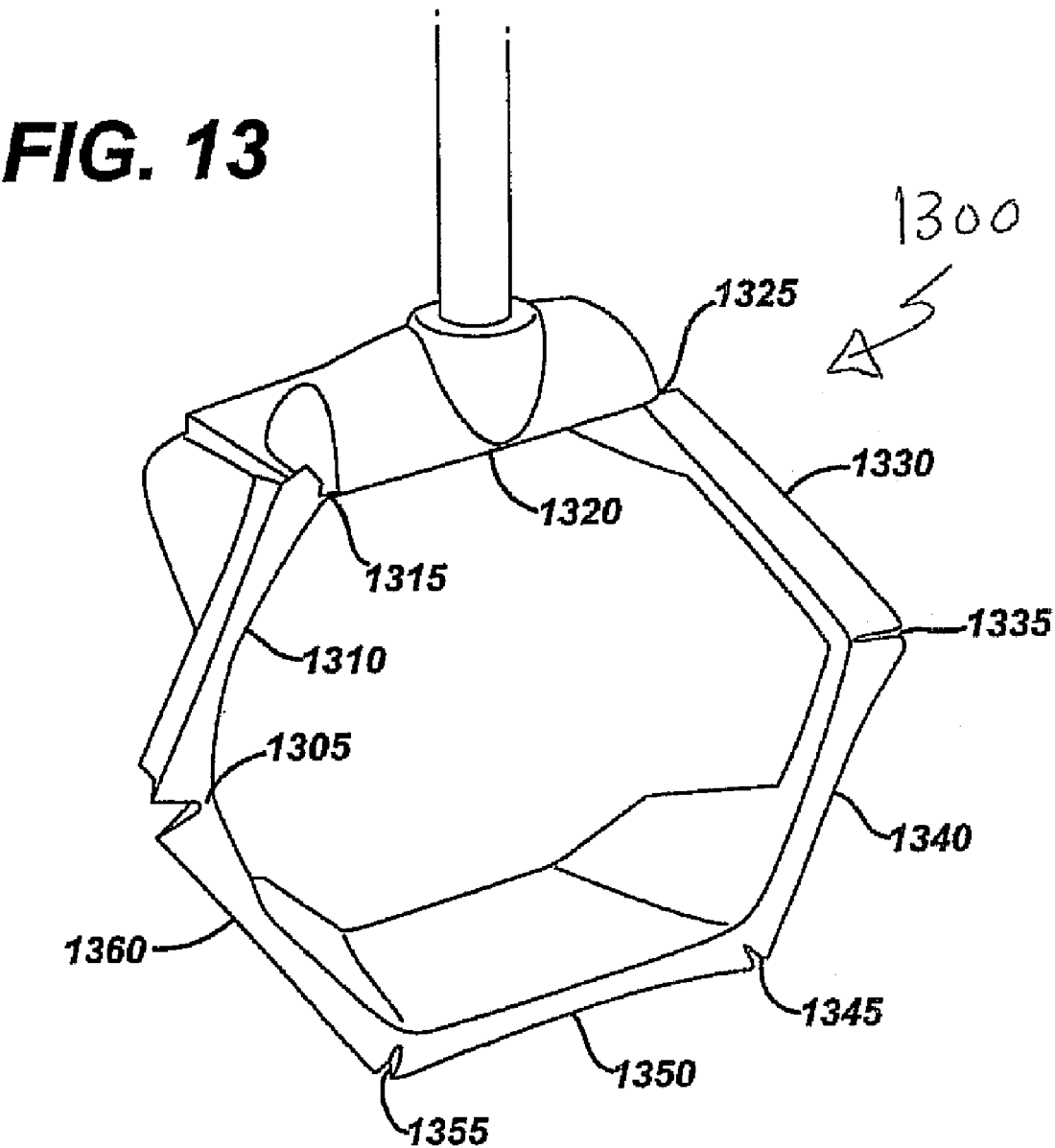
FIG. 13 shows a perspective view of a retractor with retractor blade components joined as living hinges according to a seventh embodiment of the present invention.

FIG. 13 shows a perspective view of a retractor with retractor blade components joined as living hinges according to a seventh embodiment of the present invention. The retractor 1300 includes retractor blade components 1310, 1320, 1330, 1340, 1350 and 1360 joined at living hinges 1305, 1325, 1335, 1345 and 1355. The living hinges may be formed from cutouts, e.g., notches, or otherwise weakened portions of the retractor blade components to allow neighboring retractor blade components to rotate, e.g., pivot, with respect to each other. The retractor blade components may be formed from a unitary piece of plastic, for example.

Figure 13A:
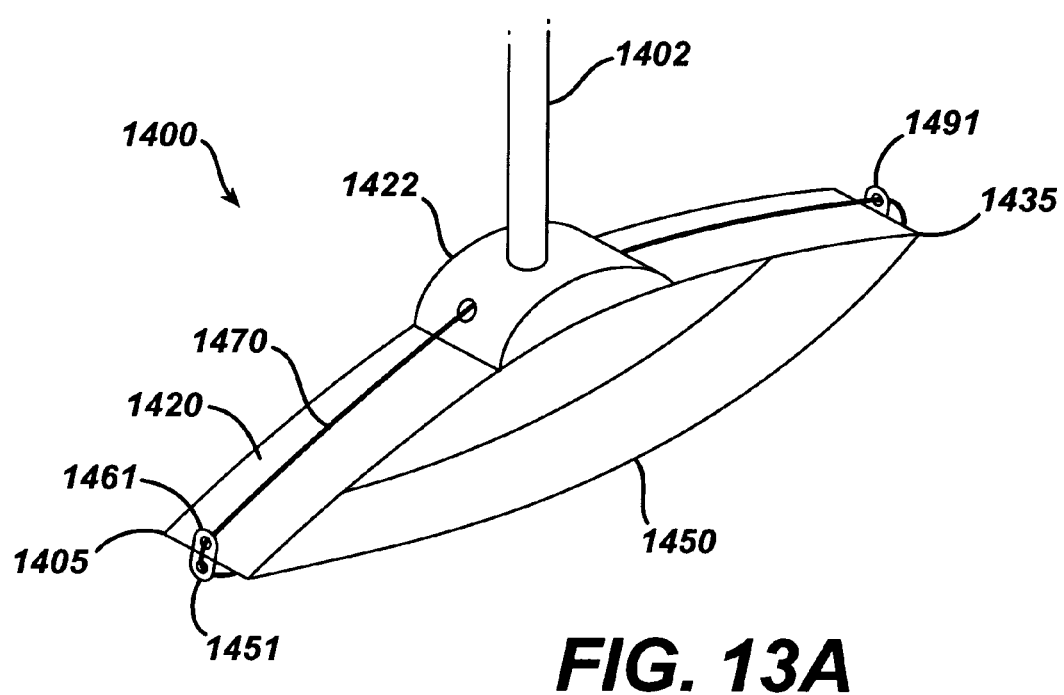
FIG. 13(A) shows a perspective view of a retractor with unitary flexible blades according to an eighth embodiment of the present invention.

FIG. 13(A) shows a perspective view of a retractor having only two flexible blade components according to an eighth embodiment of the present invention. Retractor 1400 has two unitary flexible blades 1420, 1450. Though two blades are illustrated, three or more may be used. Flexible blades 1420, 1450 may be formed of metal, plastic, elastomer, or any material exhibiting sufficient resiliency and flexibility. Additionally, more than two blades may be used. Flexible blades 1420 and 1450 are pivotally joined at pivot points 1405, 1435. A cable 1470 is routed from a winding mechanism (not shown) within raised structure 1422, through flanges 1451, 1461, 1491, and a flange not pictured, adjacent pivot point 1435 on flexible blade 1450. Also shown is a handle 1402, engaged with the raised structure 1422.

In operation, as the cable 1470 is shortened by action of the winding mechanism, flexible blades 1420, 1450 will flex outward toward a generally circular open position. Optionally, flexible blades 1420, 1450 may be biased outward at least slightly in a resting position to aid in flexing by promoting buckling of the blades. The provision of outward bias will be limited by the desire to maintain a low profile in the closed state, as explained elsewhere. Additionally, either or both of flexible blades 1420, 1450 may be curved or otherwise directed outwardly along either or both lateral edges thereof, for example as blade 1212 (FIG. 12). Alternately or additionally, they may extend laterally, as blades 120, 150 or other embodiments, discussed above.

Figure 14:
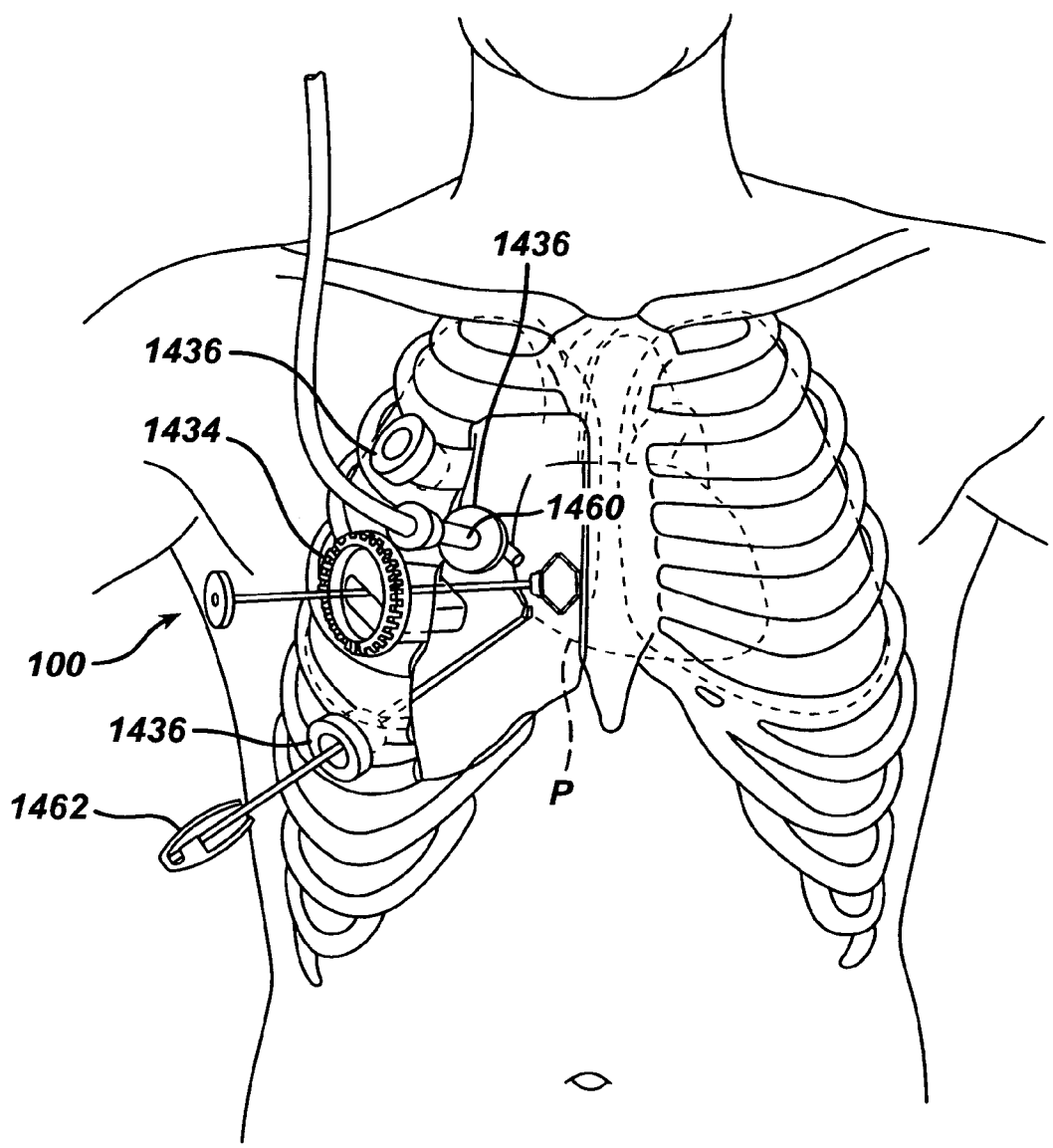
FIG. 14 shows a partial cutaway view of a patient's chest with the retractor inserted according to a surgical method of the present invention.

FIG. 14 shows a partial cutaway view of a patient's chest with the retractor inserted according to a surgical method of the present invention. In an example surgical method in which the retractor described herein may be used, a number of percutaneous cannulae or ports are positioned in incisions in the anterior chest and right lateral chest to provide access into the chest cavity. A port 1434, which may be oval, is located in the right lateral chest in the second, third, fourth, fifth or sixth intercostal space, and at least one instrument port 1436 in the right lateral chest or anterior chest is provided for introduction of instruments or visualization devices.

Instrument ports 1436 are configured for placement within an intercostal space without requiring retraction of the ribs, and are usually 5–12 mm in diameter. To introduce the ports, a small puncture or incision is made in the intercostal space at the desired location, and, with an obturator positioned in the lumen of the ports, they are advanced through the puncture or incision. The port 1434 is also configured for placement within an intercostal space without retraction of ribs, and has a width of less than about 30 mm, and preferably less than about 25 mm.

In addition to the oval configuration shown, port 1434 may have an inner lumen of various other shapes, including race-track, rectangular, trapezoidal, elliptical or circular. Alternatively, port 1434 may be made of a flexible or deformable material to allow it to be shaped by the user or to conform to the shape of the intercostal space. In addition, other means of tissue retraction may be used in place of port 1434, such as a 3-sided channel-shaped member, or a wound retractor having a pair of adjustable parallel blades which can be placed in an intercostal incision and used to create a space by widening the distance between the blades.

With ports 1434, 1436 in position, surgery within the chest cavity may begin. Much, if not all of the procedure may be carried out under direct vision by illuminating the chest cavity with a light source or light guide positioned in an instrument port or in the oval port and looking through the inner lumen of oval port 1434 or through one of the instrument ports 1436. In most cases, however, it will be desirable to introduce a thoracoscope 1460 through an instrument port 1436 to provide additional illumination and visualization of the chest cavity, preferably by means of a video camera mounted to thoracoscope 1460 which transmits a video image to a monitor. Thoracoscopic surgical instruments are then introduced to form an opening in the pericardium, which surrounds the heart. If the right lung is not sufficiently collapsed, atraumatic retraction instruments may be introduced through one of the ports to push the lung posteriorly such that the pericardium is visible by looking through oval port 1434 or through one of instrument ports 1436. Thoracoscopic scissors 1462 are then introduced through oval port 1434 or instrument port 1436 and used to cut an opening in the pericardium P.

A low profile retractor as described herein, such as retractor 100, may be introduced into the chest cavity via the port 1434, for instance. The retractor 100 may be designed to pivot on the retractor blade 120 (FIG. 1(*a*)) to allow the outer portion 230 of the handle 200 to be either in the same plane as the retractor blades in the closed position, or at some angle to that plane. The parallel position in particular allows the entire retractor to pass through the intercostal, or space between the ribs. For example, as discussed, the handle 200 may have a tongue pivotally coupled to its distal end that is received in an aperture in the winding mechanism, such as the socket 182, to achieve the parallel configuration. Generally, the retractor may be size appropriately for inserting into the body via an incision. In another approach, the retractor without the handle is entered through the thoracotomy and the handle is entered through a stab incision in the anterior chest wall near the sternum. The handle is coupled to the retractor in situ, e.g., to perform an atrial retraction.

The present invention has been described herein with reference to certain preferred embodiments. These embodiments are offered as illustrative, and not limiting, of the scope of the invention. Certain modifications or alterations may be apparent to those skilled in the art without departing from the scope of the invention, which is defined by the appended claims.

The invention claimed is:

1. A surgical retractor, comprising:
   at least two retractor blade components joined pivotally;
   a cable, a deployed length of which is guided by the at least two retractor blade components; and
   a mechanism carried by at least one of the at least two retractor blade components for shortening the deployed length of the cable to cause the at least two retractor blade components to transition between a closed position to an open position, wherein the at least two retractor blade components are joined end to end.

2. The surgical retractor of claim 1, wherein the cable is guided at least partly through at least one retractor blade component.

3. The surgical retractor of claim 1, wherein the cable is guided at least partly by structures on surfaces of at least one retractor blade component.

4. The surgical retractor of claim 1, wherein the mechanism comprises a rotatable spool to which at least one end of the cable is attached.

5. The surgical retractor of claim 1, wherein the mechanism comprises dual posts about which the cable is wound.

6. The surgical retractor of claim 1, further comprising a ratchet mechanism for winding the mechanism.

7. The surgical retractor of claim 1, further comprising an elongated handle operatively connected to the mechanism.

8. The surgical retractor of claim 7, wherein the elongated handle is detachable from the mechanism.

9. The surgical retractor of claim 7, wherein the elongated handle is secured to one of the at least two retractor blade components using at least one ball and cup-shaped recess.

10. The surgical retractor of claim 1, further comprising springs for biasing the at least two retractor blade components toward the closed position.

11. The surgical retractor of claim 10, wherein the springs are located at least where opposing sides of the surgical retractor are pivotally joined.

12. The surgical retractor of claim 1, wherein the at least two retractor blade components are each unitary.

13. The surgical retractor of claim 1, wherein the at least two retractor blade components are injection molded.

14. The surgical retractor of claim 1, wherein the at least two retractor blade components are ranged in opposing sides of the surgical retractor that are substantially parallel to one another when in the closed position.

15. The surgical retractor of claim 1, wherein at least a portion of at least one of the at least two retractor blade components comprises a malleable material.

16. The surgical retractor of claim 1, wherein the at least two retractor blade components are pivotally fixed together.

17. The surgical retractor of claim 1, wherein the at least two retractor blade components are pivotally joined by at least one living hinge.

18. The surgical retractor of claim 1, wherein at least one of the at least two retractor blade components comprises a portion that slopes radially inward toward a base end of the at least one of the at least two retractor blade components to assist in holding retracted tissue.

19. The surgical retractor of claim 1, wherein lengths of the at least two retractor blade components are not all equal.

20. The surgical retractor of claim 1, wherein the retractor blade components are pivotally joined at pivot points, and when the retractor transitions from the closed position to the open position, pivot points that join opposing sides of the retractor move radially inward, while remaining pivot points move radially outward.

21. The surgical retractor of claim 1, wherein the at least two retractor blade components are flexible retractor blades.

22. The surgical retractor of claim 21, wherein one flexible retractor blade is biased outwardly to promote bukling.

23. A surgical retractor, comprising:
   at least two banks of retractor blades, each of the at least two banks of retractor blades comprised of a plurality of articulated blade members comprising a deformable bio-compatible material;
   a cable, a deployed length of which is at least partially guided by each of the at least two banks of retractor blades; and
   a mechanism carried by at least one of the at least two banks of retractor blades for shortening the deployed length of the cable to cause the at least two banks of retractor blades to deform between a closed position to an open position, wherein the at least two banks of retractor blades are arc-shaped.

24. The surgical retractor of claim 23, wherein the at least two banks of retractor blades are positioned substantially back to back in the closed position.

25. The surgical retractor of claim 23, wherein the cable extends lengthwise at least partially through a midpoint of each of the at least two banks of retractor blades.

26. The surgical retractor of claim 23, wherein:
   the cable comprises first and second cables, deployed lengths of which extend at least partially lengthwise through each of the at least two banks of retractor blades; and
   the mechanism is adapted to shorten the deployed length of the first and second cables together to cause the at least two banks of retractor blades to deform from the closed position to the open position.

27. The surgical retractor of claim 23, wherein for at least one of the at least two banks of retractor blades, the retractor blades are separated by living hinges which allow the at least one of the at least two banks of retractor blades to deform.

28. The surgical retractor of claim 23, wherein the mechanism comprises a threaded member that engages one of the at least two banks of retractor blades.

29. A surgical method, comprising:
   inserting a retractor in a closed position into a body though a first incision in the body;
   wherein the retractor includes at least two retractor blade components joined pivotally, a cable, a deployed length of which is guided by the at least two retractor blade components, and a mechanism carried by at least one of the at least two retractor blade components; and
   operating the mechanism between a portion of a handle that is outside the body, where the handle is coupled to the mechanism, to shorten the deployed length of the cable to cause the at least two retractor blade components to transition from the closed position to an open position, further comprising coupling the handle to the retractor after the retractor is inserted into the body.

30. The surgical method of claim 29, wherein an atrial retraction is performed when the at least two retractor blade components transition from the closed position to the open position.

31. The surgical method of claim 29, wherein the handle is inserted into the body through a second incision in the body.

32. The surgical method of claim 29, wherein the first incision is between ribs of the body.

33. A surgical method, comprising:
positioning a retractor in an at least partially closed position for retracting tissue of a body;
wherein the retractor includes at least two retractor blade components joined pivotally, a cable, a deployed length of which is guided by the at least two retractor blade components, a mechanism carried by at least one of the at least two retractor blade components, and a handle coupled to the mechanism, the at least two retractor blade components being joined end to end; and
operating the mechanism using the handle to shorten the deployed length of the cable to cause the at least two retractor blade components to transition from the closed position to an open position to refract the tissue.

* * * * *